US012606831B2

(12) United States Patent
Li et al.

(10) Patent No.: US 12,606,831 B2
(45) Date of Patent: Apr. 21, 2026

(54) METHOD FOR PRODUCING T CELLS MODIFIED BY CHIMERIC ANTIGEN RECEPTOR

(71) Applicant: HEBEI SENLANG BIOTECHNOLOGY CO., LTD, Hebei (CN)

(72) Inventors: Jianqiang Li, Hebei (CN); Qinglong Wang, Hebei (CN); Lin Wang, Hebei (CN)

(73) Assignee: Hebei Senlang Biotechnology Co., Ltd., Hebei (CN)

(*) Notice: Subject to any disclaimer, the term of this patent is extended or adjusted under 35 U.S.C. 154(b) by 1215 days.

(21) Appl. No.: 17/054,043

(22) PCT Filed: Jan. 18, 2019

(86) PCT No.: PCT/CN2019/072285
§ 371 (c)(1),
(2) Date: Nov. 9, 2020

(87) PCT Pub. No.: WO2019/214290
PCT Pub. Date: Nov. 14, 2019

(65) Prior Publication Data
US 2021/0154231 A1 May 27, 2021

(30) Foreign Application Priority Data
May 9, 2018 (CN) .......................... 201810436500.8

(51) Int. Cl.
| | |
|---|---|
| *C12N 15/113* | (2010.01) |
| *A61K 40/11* | (2025.01) |
| *A61K 40/31* | (2025.01) |
| *A61K 40/42* | (2025.01) |
| *C12N 5/0783* | (2010.01) |
| *C12N 5/0784* | (2010.01) |
| *C12N 15/115* | (2010.01) |
| *C12N 15/85* | (2006.01) |

(52) U.S. Cl.
CPC ............ *C12N 15/115* (2013.01); *A61K 40/11* (2025.01); *A61K 40/31* (2025.01); *A61K 40/4211* (2025.01); *A61K 40/4212* (2025.01); *C12N 5/0636* (2013.01); *C12N 5/0639* (2013.01); *C12N 15/85* (2013.01); *C12N 2310/531* (2013.01); *C12N 2501/2302* (2013.01); *C12N 2502/30* (2013.01); *C12N 2740/15041* (2013.01)

(58) Field of Classification Search
CPC ..................... C12Q 2600/178; A61K 31/7088
See application file for complete search history.

(56) References Cited

U.S. PATENT DOCUMENTS

| | | | |
|---|---|---|---|
| 2017/0233454 A1* | 8/2017 | Li | C07K 19/00 424/134.1 |
| 2018/0125889 A1* | 5/2018 | Leek | A61K 39/4611 |

FOREIGN PATENT DOCUMENTS

| | | | |
|---|---|---|---|
| CN | 101679466 A | 3/2010 | |
| CN | 105112370 A | 12/2015 | |
| CN | 105848484 A | 8/2016 | |
| CN | 107208061 A | 9/2017 | |
| CN | 107771215 A | 3/2018 | |
| CN | 108588023 A | 9/2018 | |
| WO | 2006039721 A2 | 4/2006 | |
| WO | WO-2016201394 A1 * | 12/2016 | A61K 35/15 |

OTHER PUBLICATIONS

D'Asaro (The Journal of Immunology, vol. 184, No. 6, p. 3260-3268, 2010) (Year: 2010).*

Li, Jiangqian et al. "Reduced Expression of the Mevalonate Pathway Enzyme Farnesyl Pyrophosphate Synthase Unveils Recognition of the Tumor Cells by T Cells" The Journal of Immunology, vol. 182, Dec. 31, 2009.

Office Action issued to Application No. CN 201810436500.8 on Oct. 11, 2019.

Office Action issued to Application No. CN 201810436500.8 on Nov. 20, 2019.

"Recent progress on human γδ T cells based tumor immunotherapy" Chinese Bulletin of Life Sciences, vol. 29, No. 9, Sep. 2017.

* cited by examiner

*Primary Examiner* — Michael Allen
(74) *Attorney, Agent, or Firm* — McNees Wallace & Nurick

(57) ABSTRACT

A method for producing γδ T cells modified by a chimeric antigen receptor, comprising: transfecting K562 cells with shFPPS targeted to FPP synthase by means of a lentiviral vector, such that the expression of FPPS in the K562 cells is lowered and a K562-shFPPS cell line with reduced FPPS expression is constructed; adding the K562-shFPPS cell line into a γδ T cell culture system for co-culturing with the γδ T cells, wherein it is found that the K562-shFPPS cell line can facilitate in vitro differentiation and proliferation of the γδ T cells; and adding a CAR-expressing lentiviral vector to the γδ T cell culture system comprising the cell line for co-culturing, wherein it is found that the K562-shFPPS cell line can further effectively improve the transfection rate of CAR genes. The provided solution effectively overcomes the technical challenge of the large-scale production of CAR-γδ T cells, and has a good application prospect.

9 Claims, 9 Drawing Sheets
Specification includes a Sequence Listing.

RRE cPPT

U6 Promoter

Step 1 Add shRNA

Terminator

Step 2 Add marker

WPRE

ΔU3/3' LTR

SV40 early pA

Ampicilin

PUC ori

RSV Promoter

Δ5' LTR

ψ

SEQUENCE LISTING

```
<160> NUMBER OF SEQ ID NOS: 5

<210> SEQ ID NO 1
<211> LENGTH: 48
<212> TYPE: DNA
<213> ORGANISM: Artificial Sequence
<220> FEATURE:
<223> OTHER INFORMATION: shRNA

<400> SEQUENCE: 1
cctaaggtta agtcgccctc gctcgagcga gggcgactta accttagg                48

<210> SEQ ID NO 2
<211> LENGTH: 48
<212> TYPE: RNA
<213> ORGANISM: Artificial Sequence
<220> FEATURE:
<223> OTHER INFORMATION: shRNA

<400> SEQUENCE: 2
ccuaagguua agucgcccuc gcucgagcga gggcgacuua accuuagg                48

<210> SEQ ID NO 3
<211> LENGTH: 480
<212> TYPE: PRT
<213> ORGANISM: Artificial Sequence
<220> FEATURE:
<223> OTHER INFORMATION: CAR

<400> SEQUENCE: 3

Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30
```

```
Leu Val Lys Pro Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
        50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
                100                 105                 110

Pro Glu Asp Thr Ala Val Tyr Tyr Cys Ala Arg Glu Val Thr Gly Asp
        115                 120                 125

Leu Glu Asp Ala Phe Asp Ile Trp Gly Gln Gly Thr Met Val Thr Val
        130                 135                 140

Ser Ser Gly Gly Gly Gly Ser Asp Ile Gln Met Thr Gln Ser Pro Ser
145                 150                 155                 160

Ser Leu Ser Ala Ser Val Gly Asp Arg Val Thr Ile Thr Cys Arg Ala
                165                 170                 175

Ser Gln Thr Ile Trp Ser Tyr Leu Asn Trp Tyr Gln Gln Arg Pro Gly
                180                 185                 190

Lys Ala Pro Asn Leu Leu Ile Tyr Ala Ala Ser Ser Leu Gln Ser Gly
        195                 200                 205

Val Pro Ser Arg Phe Ser Gly Arg Gly Ser Gly Thr Asp Phe Thr Leu
        210                 215                 220

Thr Ile Ser Ser Leu Gln Ala Glu Asp Phe Ala Thr Tyr Tyr Cys Gln
225                 230                 235                 240

Gln Ser Tyr Ser Ile Pro Gln Thr Phe Gly Gln Gly Thr Lys Leu Glu
                245                 250                 255

Ile Lys Thr Thr Pro Ala Pro Arg Pro Pro Thr Pro Ala Pro Thr Ile
                260                 265                 270

Ala Ser Gln Pro Leu Ser Leu Arg Pro Glu Ala Cys Arg Pro Ala Ala
        275                 280                 285

Gly Gly Ala Val His Thr Arg Gly Leu Asp Phe Ala Cys Asp Ile Tyr
        290                 295                 300

Ile Trp Ala Pro Leu Ala Gly Thr Cys Gly Val Leu Leu Leu Ser Leu
305                 310                 315                 320

Val Ile Thr Leu Tyr Cys Lys Arg Gly Arg Lys Lys Leu Leu Tyr Ile
                325                 330                 335

Phe Lys Gln Pro Phe Met Arg Pro Val Gln Thr Thr Gln Glu Glu Asp
                340                 345                 350

Gly Cys Ser Cys Arg Phe Pro Glu Glu Glu Glu Gly Gly Cys Glu Leu
        355                 360                 365

Arg Val Lys Phe Ser Arg Ser Ala Asp Ala Pro Ala Tyr Lys Gln Gly
        370                 375                 380

Gln Asn Gln Leu Tyr Asn Glu Leu Asn Leu Gly Arg Arg Glu Glu Tyr
385                 390                 395                 400

Asp Val Leu Asp Lys Arg Arg Gly Arg Asp Pro Glu Met Gly Gly Lys
                405                 410                 415

Pro Arg Arg Lys Asn Pro Gln Glu Gly Leu Tyr Asn Glu Leu Gln Lys
                420                 425                 430

Asp Lys Met Ala Glu Ala Tyr Ser Glu Ile Gly Met Lys Gly Glu Arg
        435                 440                 445
```

-continued

```
Arg Arg Gly Lys Gly His Asp Gly Leu Tyr Gln Gly Leu Ser Thr Ala
    450                 455                 460

Thr Lys Asp Thr Tyr Asp Ala Leu His Met Gln Ala Leu Pro Pro Arg
465                 470                 475                 480

<210> SEQ ID NO 4
<211> LENGTH: 1380
<212> TYPE: DNA
<213> ORGANISM: Artificial Sequence
<220> FEATURE:
<223> OTHER INFORMATION: CAR

<400> SEQUENCE: 4
atgctgctgc tcgtgacatc tctgctgctg tgcgagctgc cccacccgc ctttctgctg       60 attcctcagg tgcagctgca gcagtctggc cctggcctcg tgaagcctag ccagaccctg      120
agcctgacct gtgccatcag cggcgatagc gtgtccagca atagcgccgc ctggaactgg      180
atcagacaga gccctagcag aggcctggaa tggctgggcc ggacctacta ccggtccaag      240
tggtacaacg actacgccgt gtccgtgaag tcccggatca ccatcaaccc cgacaccagc      300
aagaaccagt tctccctgca gctgaacagc gtgacccccg aggataccgc cgtgtactac      360
tgcgccagag aagtgaccgg cgacctggaa gatgccttcg acatctgggg ccagggcaca      420
atggtcaccg tgtctagcgg aggcggcgga agcgacatcc agatgacaca gagccccagc      480
tccctgagcg ccagcgtggg agacagagtg accatcacct gtcgggccag ccagaccatc      540
tggtcctacc tgaactggta tcagcagcgg cctggcaagg cccccaacct gctgatctat      600
gccgccagct cactgcagag cggcgtgccc agcagatttt ccggcagagg cagcggcacc      660
gacttcaccc tgacaatcag ttccctgcag gccgaggact cgccaccta ctactgccag      720 cagagctaca gcatccccca gaccttcggc caggggacca agctggaaat caagacgacg      780
ccagcgccgc gaccaccaac accggcgccc accatcgcgt cgcagcccct gtccctgcgc      840
ccagaggcgt gccggccagc ggcggggggc gcagtgcaca cgaggggggct ggacttcgcc      900 tgtgatatct acatctgggc gcccttggcc gggacttgtg gggtccttct cctgtcactg      960
gttatcaccc tttactgcaa acggggcaga aagaaactcc tgtatatatt caaacaacca     1020
tttatgagac cagtacaaac tactcaagag gaagatggct gtagctgccg atttccagaa     1080
gaagaagaag gaggatgtga actgagagtg aagttcagca ggagcgcaga cgcccccgcg     1140
tacaagcagg gccagaacca gctctataac gagctcaatc taggacgaag agaggagtac     1200 gatgtttgg acaagagacg tggccgggac cctgagatgg ggggaaagcc gagaaggaag      1260
aaccctcagg aaggcctgta caatgaactg cagaaagata agatggcgga ggcctacagt     1320
gagattggga tgaaaggcga gcgccggagg ggcaaggggc acgatggcct ttaccagggt     1380

<210> SEQ ID NO 5
<211> LENGTH: 48
<212> TYPE: DNA
<213> ORGANISM: Artificial Sequence
<220> FEATURE:
<223> OTHER INFORMATION: Scramble-shRNA

<400> SEQUENCE: 5
ccagcagtgt tcttgcaata tctcgagata ttgcaagaac actgctgg                    48
```

METHOD FOR PRODUCING T CELLS MODIFIED BY CHIMERIC ANTIGEN RECEPTOR

PRIORITY CLAIM AND CROSS-REFERENCE TO RELATED APPLICATIONS

This application is a national stage application, filed under 35 U.S.C. § 371, of International Patent Application Serial No. PCT/CN2019/072285, filed on Jan. 18, 2019, which claims the priority benefit of the earlier filed Application Serial No. CN 201810436500.8 filed on May 9, 2018, the entirety of which are incorporated by reference herein.

TECHNICAL FIELD

The present disclosure relates to the field of biotechnology, and in particular, to a method for producing γδ T cells modified by a chimeric antigen receptor.

BACKGROUND

The adoptive cellular immunotherapy is to transfuse autologous or allogeneic immune cells cultured, activated and genetically modified in vitro to the patient to exert the antitumor activity. The chimeric antigen receptor (CAR)-modified T cell therapy technology (CAR-T technology) is to modify immune effector cells through the genetic engineering technology such that the modified cells can specifically recognize and kill target cells expressing specific antigens, so as to achieve the purpose of specific elimination of tumor cells. The CAR-T cells that specifically target the CD19 molecule, a surface marker of B lymphocytes, have presented the most significant therapeutic effects in the treatment of B lymphocyte malignant tumors, enabling 90% of patients with relapsed and/or refractory B lineage acute lymphoblastic leukemia to obtain complete remission. Although the treatment method of using CAR-T cells against the CD19 antigen for the treatment of B-lymphocyte tumors has an extremely high short-term therapeutic effect, there are still a considerable number of patients who would suffer a relapse after the treatment has reached complete remission. An essential reason for the relapse is that the number of infused CAR-T cells in the patient's body is declining due to the lack of effective antigen stimulation, and thus the long-term anti-tumor activity cannot be maintained.

The existing CAR-T technology is designed based on the natural activity of αβ T cells, in which modified effector cells are generally αβ T cells. The infusion of αβ T cells into allogeneic organisms will cause severe graft-versus-host reactions. Therefore, the current CAR-T treatment technology is mostly autologous cell therapy, which, however, greatly limits clinical application flexibility and greatly increases treatment costs. On the contrary, γδ T cells will not cause serious graft-versus-host reactions, so they are a better choice to develop universal CAR-T products.

It is the adaptive immune response that αβ T cells mediate, which requires the completion of lymphocyte recirculation to effectively activate and exert corresponding immunological functions. While what γδ T cells mediate is the natural immune response, which can immediately exert immunological effects at the site where the antigen and antibody react. Therefore, the potential anti-tumor effect of CAR-γδ T cells will be more direct and rapid, and the tumor can be eliminated by performing local injection on the tumor site, avoiding strong adverse reactions caused by off-target effects. In addition, αβ T cells use diverse αβ TCRs to recognize short antigen peptides presented by the major histocompatibility complex (MHC). Naturally, the number of αβ T cells that recognize a specific MHC-antigen peptide complex is very small, so the number of such αβ T cells needs to be amplified to give full play to the immune response to a specific antigen. However, γδ T cells are T lymphocyte subpopulations with the relatively low number, and most γδ TCRs recognize non-peptide compounds without the MHC presentation. Unlike the diversity composition of the variable region of the αβ TCR, the diversity of the variable region of the γδ TCR is very limited. Therefore, although the total number of αβ T cells is much greater than that of γδ T cells, in terms of the number of specific T cells that have the ability to recognize a specific compound or antigen, the number of γδ T cells is higher than that of αβ T cells.

The γδ T cells of humans and other primates mainly include two subtypes, Vδ1 and Vγ9δ2, which respectively represent the types of TCR expressed on the surface. Vδ1 is distributed in tissues, and the peripheral γδ T cells are mainly a Vγ9δ2 subclass. The antigen recognition modes of these two types of cells are completely different. The types of antigens recognized by the Vδ1 TCR are currently controversial. Vγ9δ2 TCR recognizes its own or exogenous small molecule phosphorylated antigens, such as HMBPP (bacterial origin), IPP (human origin) and BrHPP (artificial synthesis) (Chen, Z. W. and N. L. Letvin, 2003. 5(6): p. 491-8; Eberl, M., et al., 2003. 544(1-3): p. 4-10; Kabelitz, D., D. Wesch, and W. He, 2007. 67(1): p. 5-8; Sireci, G., et al., 2001. 31(5): p. 1628-35). Amino-Bisphosphonate compound drugs, Zoledronate (Zol) and Pamidornate, can inhibit FPP synthase (FPPS), thereby inhibiting the metabolic pathway of HMG-CoA and resulting in the accumulation of downstream products IPP in vivo or in cells, and such that these drugs can effectively stimulate and activate Vγ9δ2 T cells in vivo and in vitro (Kunzmann, V. and M. Wilhelm, 2005. 46(5): p. 671-80).

Although the natural activity of γδ T cells makes them an excellent carrier for the CAR-T cell therapy, there is no report on successful clinical application of CAR-modified γδ T cells due to limitations such as low cell content, difficulty in large-scale amplification in vitro, and low transfection rate. The conventional in vitro γδ T cell amplification techniques, including solid-phase anti-pan TCR γδ antibody amplification or selective amplification of Vγ9δ2T cells with IPP/HMBPP/ZOL, are all to perform amplification from peripheral mononuclear cells (PBMCs), and due to the low proportion of γδ T cells, the gene transfection is interfered by other unrelated cells, resulting in the low transfection rate. Furthermore, the final product amplified from PBMCs has low purity and is easy to be mixed with αβ T cells, which is not conducive to the development of universal CAR-T products. The sorting and purifying of γδ T cells can solve the above problems, but without the assistance of other cells, the activation and amplification efficiency will be greatly reduced.

SUMMARY

The technical problem to be solved in the present disclosure is how to improve the amplification efficiency of γδ T cells, so as to realize the large-scale production of CAR-γδ T cells for clinical tumor immunotherapy.

To solve the above technical problem, the present disclosure first provides a method for amplifying γδ T cells.

The method for amplifying γδ T cells provided in the present disclosure includes a step of adding tumor cells with reduced FPPS expression and/or activity to a γδ T cell culture system.

In the above method, a ratio of the number of the γδ T cells to the number of the tumor cells with reduced FPPS expression and/or activity is (1-10):1.

Further, the ratio of the number of the γδ T cells to the number of the tumor cells with reduced FPPS expression and/or activity is 3:1.

The above method further includes the following step: adding IL-2 once to the culture system every 2-4 days when the cell concentration in the culture system reaches $(1.5-2)\times 10^6$ cells/ml, where a criterion for adding the IL-2 is that the final concentration of the IL-2 in the culture system is (100-1000) IU/mL.

Further, when the cell concentration in the culture system reaches $(1.5-2)\times 10^6$ cells/ml, the IL-2 is added once to the culture system every 3 days, where the criterion for adding the IL-2 is that the final concentration of the IL-2 in the culture system is (100-300) IU/mL.

Even further, when the cell concentration in the culture system reaches $(1.5-2)\times 10^6$ cells/ml, the IL-2 is added once to the culture system every 3 days, where the criterion for adding the IL-2 is that the final concentration of the IL-2 in the culture system is 200 IU/mL.

To solve the above technical problem, the present disclosure further provides a method for producing CAR-γδ T cells.

The method for producing CAR-γδ T cells provided in the present disclosure includes the following step: co-culturing a vector expressing a chimeric antigen receptor (CAR) with γδ T cells to obtain CAR-γδ T cells, where the culture system contains tumor cells with reduced FPPS expression and/or activity.

In the above method, the method of co-culturing a vector expressing a chimeric antigen receptor with γδ T cells includes the following steps:

1) adding the tumor cells with reduced FPPS expression and/or activity to a γδ T cell culture system and culturing to obtain a culture system; and 2) adding the vector expressing the chimeric antigen receptor to the culture system and culturing to obtain the CAR-γδ T cells.

In the above method, in the step 1), the ratio of the number of the γδ T cells to the number of the tumor cells with reduced FPPS expression and/or activity is (1-10):1.

Further, the ratio of the number of the γδ T cells to the number of the tumor cells with reduced FPPS expression and/or activity is 3:1.

In the above method, in the step 1), the culturing conditions are as follows: culturing for 2 days in 5% $CO_2$ at 37° C.

In the above method, in the step 1), the γδ T cell culture system is composed of a TexMACS™ medium and recombinant human IL-2, and the concentration of the recombinant human IL-2 in the γδ T cell culture system is 200 U/ml.

In the above method, the step 2) further includes the following step: adding IL-2 once to the culture system every 2-4 days when the cell concentration in the culture system reaches $(1.5-2)\times 10^6$ cells/ml, where the criterion for adding the IL-2 is that the final concentration of the IL-2 in the culture system is (100-1000) IU/mL.

Further, when the cell concentration in the culture system reaches $(1.5-2)\times 10^6$ cells/ml, the IL-2 is added once to the culture system every 2 days, where the criterion for adding the IL-2 is that the final concentration of the IL-2 in the culture system is (100-300) IU/mL.

Even further, when the cell concentration in the culture system reaches $(1.5-2)\times 10^6$ cells/ml, the IL-2 is added once to the culture system every 2 days, where the criterion for adding the IL-2 is that the final concentration of the IL-2 in the culture system is 200 IU/mL.

In the above method, in the step 2), the culturing conditions are as follows: culturing for 10-14 days in 5% $CO_2$ at 37° C.

In the above method, in the step 2), the vector expressing the chimeric antigen receptor is a lentiviral vector expressing the chimeric antigen receptor.

Before the lentiviral vector expressing the chimeric antigen receptor is added to the culture system, the method further includes a step of packaging. The packaging method can be specifically carried out according to the following steps: 2-1) adding $4.5\times 10^6$ 293FT cells and 9 mL of DMEM complete medium to each cell culture dish, mixing them well, and putting the mixture into a cell incubator for culturing; 2-2) on the second day of culturing, adding the following reagents to each culture dish: 500 μL of jetPRIME® buffer, 6 μg of lentiviral vectors expressing the chimeric antigen receptor, 3 μg of psPAX2 and 1.5 μg of pMD2.G, mixing them well, then adding jetPRIME® to the system at 25 μL per 10 cm-culture dish, mixing them again, and letting the mixture stand at room temperature for 10 min to obtain a mixed solution; 2-3) taking the 293FT cells used for packaging viruses out of the cell incubator, adding the mixed solution to each culture dish, mixing the cells and the mixed solution well, and putting them into the cell culture incubator for continuous culturing; after 4 h of culturing, discarding the old medium, adding PBS to wash the cells, adding a DMEM complete medium containing 10% (volume fraction) FBS, and putting them in the cell incubator for culturing; and 2-4) after 48-72 h of culturing, collecting the culture supernatant as the virus stock, filtering the collected virus stock into a centrifuge tube, centrifuging the virus stock, discarding the supernatant, and adding a DMEM complete medium to the precipitate (the volume ratio of the added medium to the virus stock is 1:500) to resuspend viral particles to obtain lentiviral particles expressing the chimeric antigen receptor.

After the lentiviral vector expressing the chimeric antigen receptor is added to the culture system, the method further includes a step of centrifugation.

The centrifugation conditions specifically may be: centrifuging for 2 h at 2000 rpm at 35° C.

Further, the lentiviral vector expressing the chimeric antigen receptor is obtained by inserting a coding gene of the chimeric antigen receptor between multiple cloning sites of a lentiviral expression vector. The lentiviral expression vector may be a lentiviral expression vector commonly used in the art.

Even further, the lentiviral expression vector is Senl_pLenti-EF1. The lentiviral vector expressing the chimeric antigen receptor is a vector obtained by inserting the coding gene of the chimeric antigen receptor between restriction enzyme sites PacI and SpeI of the lentiviral expression vector Senl_pLenti-EF1.

The Senl_pLenti-EF1 vector is a vector obtained by adding restriction enzyme sites PacI and SpeI on both sides of the cloning site of an original plasmid whose name is LV-pRRLEF1.WPRE (purchased from Cyagen Biosciences Inc.).

In the above method, the tumor antigen targeted by the chimeric antigen receptor includes, but is not limited to, CD19, CD20, CD22, CD30, HER2, GD2, EGFR, EGFRvIII, EphA2, IL13Ra2, CD133, ROR1, IGF1R and/or L1CAM.

In specific examples of the present disclosure, the chimeric antigen receptor targets the tumor antigen CD22; and an amino acid sequence of the chimeric antigen receptor targeting the tumor antigen CD22 is SEQ ID No. 3 in the sequence list, and a coding gene sequence thereof is SEQ ID No. 4 in the sequence list.

To solve the above technical problem, the present disclosure further provides a method for tumor immunotherapy.

The method for tumor immunotherapy provided by the present disclosure includes the following steps:

(1) producing CAR-γδ T cells according to the above method; and (2) transfusing the CAR-γδ T cells into a tumor patient, and recognizing and killing the tumor cells in the tumor patient through the CAR-γδ T cells, thereby achieving the purpose of the tumor immunotherapy.

To solve the above problem, the present disclosure finally provides a product.

The active constituent of the product provided by the present disclosure is tumor cells with reduced FPPS expression and/or activity.

The function of the product is any one of B1) to B5):

B1) to promote γδ T cell amplification;

B2) to promote γδ T cell differentiation;

B3) to produce CAR-γδ T cells;

B4) to improve a transfection rate of lentivirus to γδ T cells; and

B5) to perform tumor immunotherapy.

In the above method or product, the tumor cells with reduced FPPS expression and/or activity are obtained by introducing a substance that inhibits expression of FPPS-encoding gene into tumor cells.

Further, the substance that inhibits the expression of FPPS-encoding gene is introduced into the tumor cells through a lentiviral vector.

Even further, the substance that inhibits the expression of FPPS-encoding gene is shRNA that inhibits the expression of FPPS-encoding gene.

In the specific examples of the present disclosure, the shRNA that inhibits the expression of FPPS-encoding gene is single-stranded RNA having a stem-loop structure formed by a stem I, a loop and a stem II.

The single-stranded RNA is shown in SEQ ID No. 2 in the sequence list; the sequence of the stem I is shown in positions 1-21 of SEQ ID No. 2 in the sequence list; the sequence of the loop is shown in positions 22-27 of SEQ ID No. 2 in the sequence list; and the sequence of the stem II is shown in positions 28-48 of SEQ ID No. 2 in the sequence list. The coding gene sequence of the single-stranded RNA is shown in SEQ ID No. 1 in the sequence list.

In the above method or product, the tumor cells may be common tumor cells, such as a chronic myelogenous leukemia cell line. In the present disclosure, the tumor cells specifically are K562 cells.

In the above method or product, the γδ T cells are Vγ9δ2 T cells. The γδ T cells are γδ-positive T cells sorted from PBMCs.

DETAILED DESCRIPTION

Experimental methods applied in the following examples are conventional methods without otherwise specified.

All the materials and reagents applied in the following examples are commercially available unless otherwise specified.

Example 1 Method for Amplifying γδ T Cells

I. Construction of a K562-shFPPS Tumor Cell Line with Reduced FPPS Expression

1. Construction of Recombinant Lentivirus Plasmids (1) Preparation of Recombinant Plasmids The recombinant lentivirus plasmids were constructed by using the U6-based shRNA construction system of the Vectorbuilder system manufactured by Cyagen Biosciences Inc.

Specific steps are as follows.

A shRNA coding sequence (shFPPS) specifically targeting FPPS was designed and synthesized as the experimental group: CCTAAGGT-TAAGTCGCCCTCGCTCGAGCGAGGGCGACT-TAACCTTAGG (SEQ ID No. 1), in which the 6 bp sequence in bold in the middle was a stem-loop sequence, 21 bp on the left of the stem-loop sequence was a sense sequence, and the 21 bp sequence on the right of the stem-loop sequence was an antisense sequence. Meanwhile, the following Scramble-shRNA coding sequence (shSRB) was synthesized as the negative control group: CCAGCAGTGTTCTTGCAATATCTCGAGATAT- TGCAAGAACACTGCTGG (SEQ ID No. 5), in which the 6 bp sequence in bold in the middle was a stem-loop sequence, 21 bp on the left of the stem-loop sequence was a sense sequence, and the 21 bp sequence on the right of the stem-loop sequence was an antisense sequence.

Figure 1:
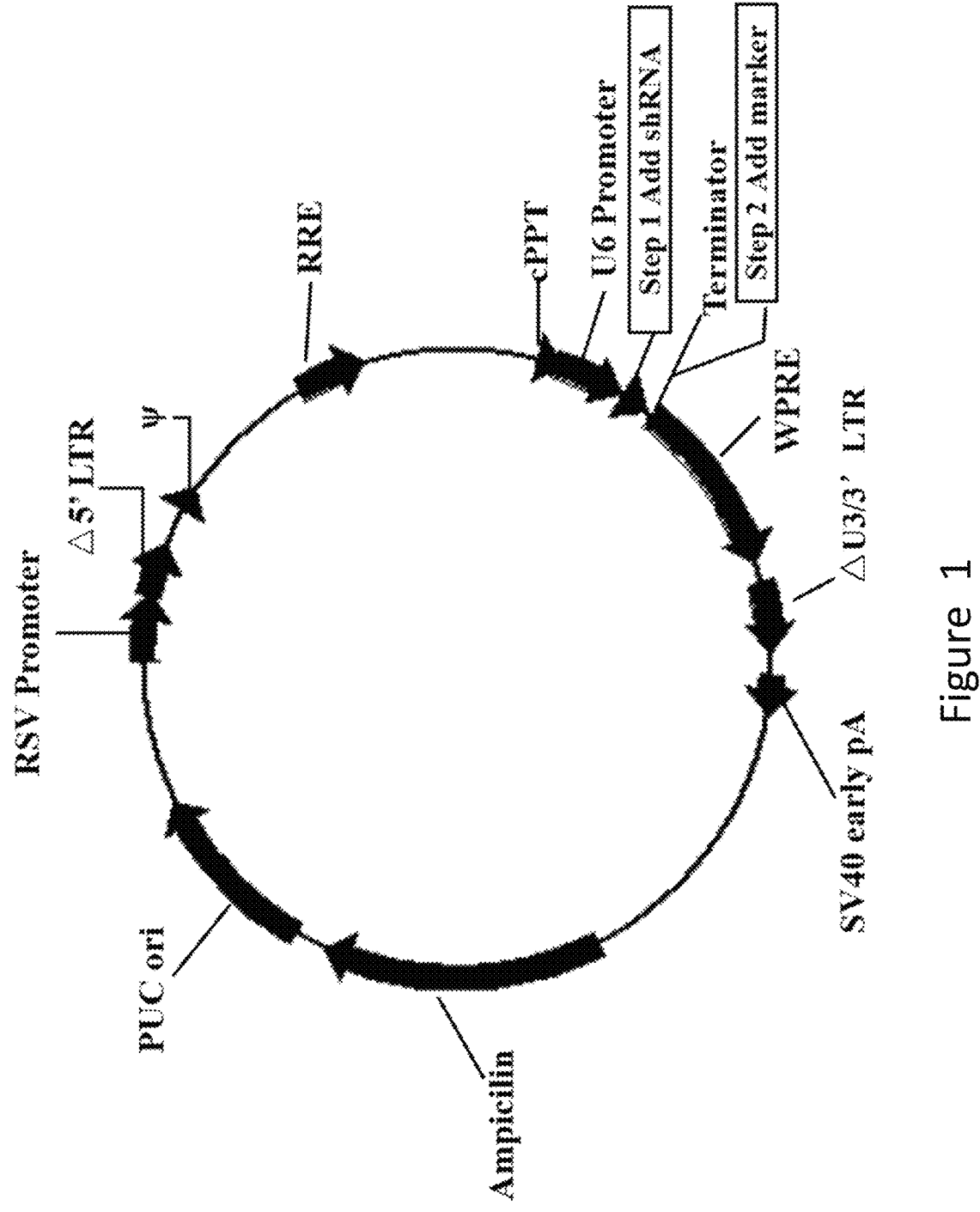
FIG. 1 shows the structure of the U6-based shRNA lentivirus plasmid.

The above shRNA coding sequences were synthesized and then cloned to under the U6 promoter of the U6-Based shRNA Knockdown lentivirus plasmid (purchased from Cyagen Biosciences Inc., catalog No.: LV-SGFP-0102), to obtain recombinant plasmids shFPPS and shSRB, respectively. In addition, the Neumycine resistance gene was introduced into the recombinant plasmids shFPPS and shSRB for positive cell screening. The structure of the recombinant plasmids is as shown in FIG. 1.

(2) Identification of Recombinant Plasmids

The recombinant plasmids were identified by using universal primers of the U6 promoter, and the recombinant plasmid that was identified as being correct by PCR was validated by sequencing. The recombinant plasmid containing the shFPPS double-stranded DNA sequence was named recombinant lentivirus plasmid shFPPS, and the recombinant plasmid containing the shSRB double-stranded DNA sequence was named recombinant lentivirus plasmid shSRB. The RNA sequence of the shFPPS expressed by the recombinant lentivirus plasmid shFPPS was: CCUAAG-GUUAAGUCGCCCUCGCUCGAGCGAGGGCGAC-UUAACCUUAGG (SEQ ID No. 2), and this sequence was single-stranded RNA having a stem-loop structure formed by a stem I, a loop and a stem II, in which the sequence of the stem I is shown in positions 1-21 of SEQ ID No. 2 in the sequence list, the sequence of the loop is shown in positions 22-27 of SEQ ID No. 2 in the sequence list, and the sequence of the stem II is shown in positions 28-48 of SEQ ID No. 2 in the sequence list.

2. Packaging of Recombinant Lentivirus Plasmids

The recombinant lentivirus plasmids shFPPS and shSRB were packaged to obtain lentiviral particles shFPPS and shSRB, respectively. Specific steps are as follows.

(1) The 293FT cell culture flask (T175) that had reached 80%-90% was taken out from the cell incubator in 5% $CO_2$ at 37° C., the cells were collected and washed after digestion, $4.5 \times 10^6$ cells and 9 mL of DMEM complete medium (purchased from Gibco, product catalog No.: 11965-084) were added to each 10 cm-cell culture dish and gently shaken, and the resulting mixture was put in the incubator in 5% $CO_2$ at 37° C.

(2) On the second day of culturing, the following reagents were added to each culture dish: 500 µL of jetPRIME® buffer (purchased from Polyplus Transfection Co., product catalog No.: B161116), 6 µg of recombinant lentivirus plasmid, 3 µg of psPAX2 (purchased from Wuhan Miaoling Biotechnology Co., Ltd., product catalog No.: P026) and 1.5 µg of pMD2.G (purchased from Guangzhou Geneseed Biotechnology Co., Ltd., product catalog No.: 161220L08) and then mixed well, and then jetPRIME® (purchased from Polyplus Transfection Co., product catalog No.: 114-15) was added to the system at 25 µL per 10 cm-culture dish and mixed well, and the resulting mixture was left to stand at room temperature for 10 min to obtain a mixed solution.

(3) The 293FT cells used for packaging viruses were taken out of the cell incubator in 5% $CO_2$ at 37° C., the mixed solution was added to each culture dish and the shaken gently, and the resulting mixture was put in the incubator in 5% $CO_2$ at 37° C. for continuous culturing. After 4 h of culturing, the old medium was discarded, 5 mL of preheated PBS was added to wash the cells, then 9 mL of fresh preheated DMEM complete medium containing 10%

(volume fraction) FBS was added, and then the mixture was put in the incubator in 5% $CO_2$ at 37° C. for culturing.

(4) After 48-72 h of continuous culturing, the culture supernatant was collected as the virus stock solution, and the collected virus stock solution was filtered into a 50 mL centrifuge tube through a 0.45 µm filter and centrifuged at 18500 g at 4° C. for 2 h. The supernatant was discarded, DMEM complete medium (the volume ratio of the added medium to the virus stock is 1:500) was added to the precipitate to resuspend virus particles to obtain the virus concentrated solution.

(5) The virus concentrated solution was divided at 200 µL/tube, and 10 µL of virus concentrated solution was saved for virus titer determination. The divided concentrated solutions were stored in the refrigerator at −80° C.

3. Transfection of Recombinant Lentivirus Particles to Target Cells

The lentiviral particles shFPPS and shSRB were transfected to target cells to obtain tumor cells K562-shFPPS and control cells K562-shSRB, respectively. Specific steps are as follows.

(1) K562 cells were taken out of the cell incubator in 5% $CO_2$ at 37° C., and plated into a 24-well plate at $3 \times 10^5$/500 µL medium/well, with a total of 12 wells. The medium was RPMI1640 (purchased from Gibco Co., catalog No.: 22400-089)+10% (volume fraction) FBS (purchased from Excell Bio Co., catalog No.: FND500).

(2) 6 wells were selected from the 12 wells as the experimental group for lentivirus transfection, and the remaining 6 wells were taken as the control group. For the experimental group, 1‰ Protamine sulfate (purchased from Sigma Co., product catalog No.: P3369-10G) and 5 µL of shFPPS virus concentrated solution were added to each well and then gently mixed by drawing the "8" on the operating table. For the control group, 5 µL of shSRB virus concentrated solution was added.

(3) The centrifuge was preheated to 35° C., and the K562 cells added with the virus concentrated solution were placed into the centrifuge for centrifugation. The centrifugation parameters were set to 2000 rpm, 20 min, lifting for 4 times and dropping for 4 times, 2 h. After centrifugation, the cells were put into the incubator in 5% $CO_2$ at 37° C. for continuous culturing.

(4) After 48 h of culturing, the experimental group and the control group were added with G418 in three gradients: low concentration 400 µg/mL, medium concentration 800 µg/mL and high concentration 1200 µg/mL, respectively, with two wells in each group. (5) According to the color of the culture medium and cell growth, the corresponding screening medium was replaced once every 3-5 days until all cells in the control wells died, while there were still living cells in the corresponding experimental group. The living cells were collected for amplification culturing.

The results show that the best screening concentration of G418 for the K562 cells was 800 µg/mL. The amplified cells were K562 cells infected with lentiviral particles shFPPS or shSRB.

4. Detection of Changes of FPPS Protein Expression Levels of the Cells Infected by shFPPS $1.5 \times 10^6$ K562-shFPPS and K562-shSRB tumor cells screened by G418 as well as wild-type K562 cells were taken, 50 µL of cell lysis solution was added to lyse the cells after centrifugation, and changes of the FPPS protein expression level were detected by Western Blot. The antibody for detecting the FPPS protein was the rabbit anti-human FPPS polyclonal antibody available from Abgent Co., (animal No. was RB4786), and the antibody for detecting the housekeeping gene protein β-tubulin was the mouse anti-human monoclonal antibody available from BD Co., (clone ID: 5H1).

Figure 2:
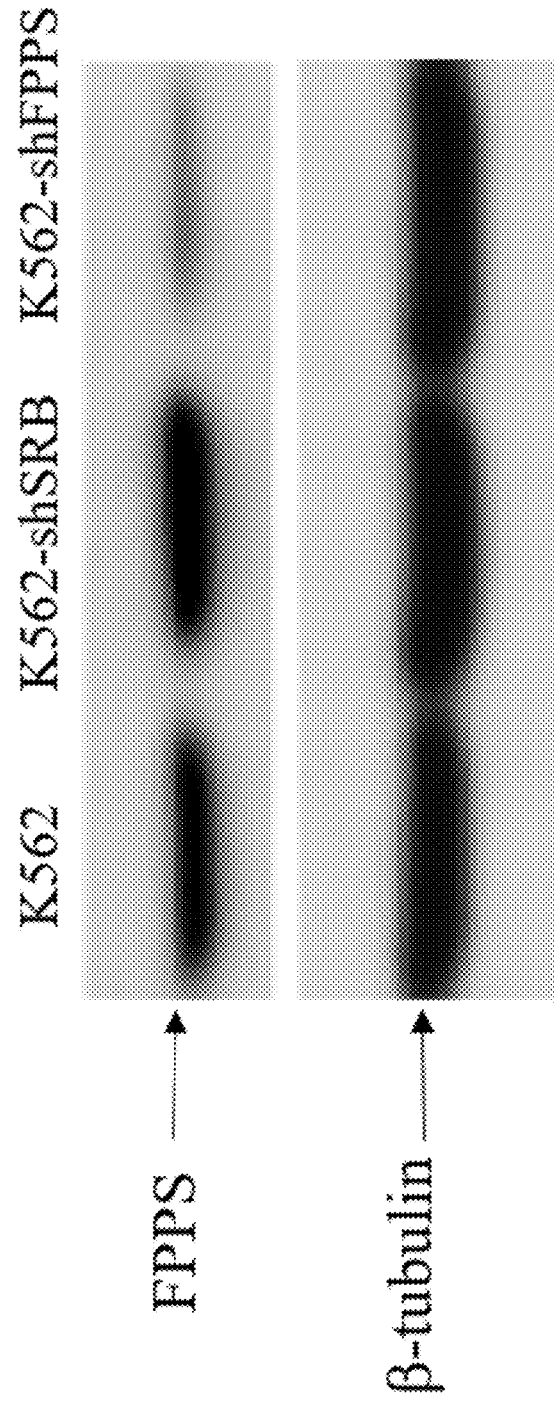
FIG. 2 shows protein expression levels of the FPPS and the housekeeping gene β-tubulin in tumor cells K562-shFPPS, K562-shSRB cells and wild-type K562 cells, detected by Western Blot.

The results are shown in FIG. 2. It can be seen from the figure that no significant difference was found between the FPPS expression level of K562-shSRB cells and that of wild-type K562 cells, while the FPPS expression level of shFPPS-expressing K562-shFPPS cells was significantly lower than that of wild-type K562 cells.

II. Method for Amplifying γδ T Cells In Vitro

1. Sorting of γδ T Cells

Figure 3:
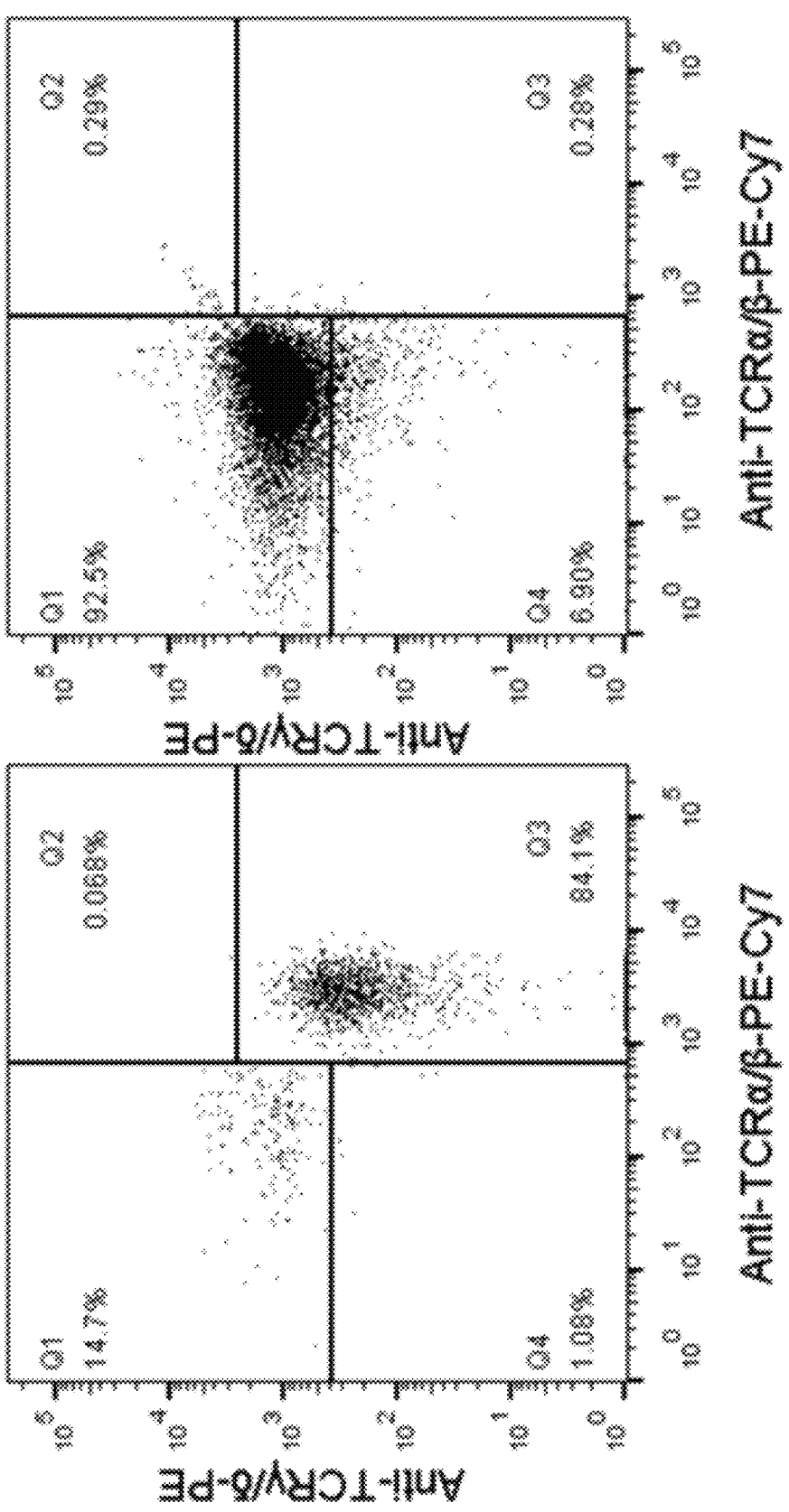
FIG. 3 shows the percentage of γδ T cells in CD3+ cells before and after γδ T cell sorting.

Freshly isolated mononuclear cells (PBMCs) derived from adult peripheral blood or umbilical cord blood were taken, and γδ T cells were sorted from PBMCs by using γδ T cell sorting kit (purchased from Miltenyi Biotechnology Co., Ltd., Germany, product catalog NO.: 130-092-892) according to the operation instructions in the specification of the kit to obtain γδ-positive T cells, and the remaining cells were γδ-negative T cells. The positive percentage of γδ T cells in the sorted γδ-positive T cells was greater than 90% (FIG. 3).

2. Labeling γδ T Cells with CFSE

36 μL of DMSO was added to the centrifuge tube containing CFSE (purchased from BioLegend Co., product catalog No.: 423801) to make the final concentration 5 mM, the mixture was pipetted up and down and mixed well, and the corresponding volume of PBS was added to make the final concentration of the CFSE solution 5 μM to obtain the CFSE working solution. $1\times10^7$-$1\times10^8$ γδ T cells (γδ-positive T cells or γδ-negative T cells in step 1) were added to 5 μL of the CFSE working solution and incubated at room temperature or 37° C. in the dark for 20 min, and 5 volumes of TexMACS™ medium (purchased from Miltenyi Biotechnology Co., Ltd., Germany, catalog No.: 130-097-196) containing 10% (volume fraction) FBS and 200 U/ml recombinant human IL-2 were added to stop staining. Centrifugation was performed at 2000 rpm for 5 min, the cells were collected, the cells were resuspended in preheated TexMACS™ medium, and then the cells were incubated at room temperature or 37° C. in the dark for 10 min. After the incubation, the cells were washed twice with preheated medium, and whether the CFSE staining was successful was detected by flow cytometry. γδ T cells successfully labeled by CESE were used in the following experiment.

3. The CFSE-labeled γδ-positive T cell suspension and the tumor cell K562-shFPPS suspension were mixed at a volume ratio of 3:1 (the ratio of the number of γδ-positive T cells to the number of tumor cells K562-shFPPS was 3:1), and then incubated in the incubator in 5% $CO_2$ at 37° C. for 72 h to obtain experimental group cells (γδ-positive T cells).

The CFSE-labeled γδ-negative T cell suspension and the tumor cell K562-shFPPS suspension were mixed at a volume ratio of 3:1 (the ratio of the number of γδ-negative T cells to the number of tumor cells K562-shFPPS was 3:1), and then incubated in the incubator in 5% $CO_2$ at 37° C. for 72 h to obtain experimental group cells (γδ-negative T cells).

The CFSE-labeled γδ-positive T cell suspension and the control tumor cell K562-shSRB suspension were mixed at a volume ratio of 3:1 (the ratio of the number of γδ-positive T cells to the number of control cells K562-shSRB was 3:1), and then incubated in the incubator in 5% $CO_2$ at 37° C. for 72 h to obtain negative control group cells (γδ-positive T cells).

The CFSE-labeled γδ-negative T cell suspension and the control tumor cell K562-shSRB suspension were mixed at a volume ratio of 3:1 (the ratio of the number of γδ-negative T cells to the number of control cells K562-shSRB was 3:1), and then incubated in the incubator in 5% $CO_2$ at 37° C. for 72 h to obtain negative control group cells (γδ-negative T cells).

The CFSE-labeled γδ-positive T cell suspension, wild-type cell K562 suspension and Zoledronate (ZOL, purchased from Roche) inhibiting FPPS were mixed, and then incubated in the incubator in 5% $CO_2$ at 37° C. for 72 h to obtain positive control group cells (γδ-positive T cells). The ratio of the number of CFSE-labeled γδ-positive T cells to the number of K562 cells was 3:1, and the final concentration of Zoledronate in the culture system was 5 μM.

The CFSE-labeled γδ-negative T cell suspension, wild-type cell K562 suspension and Zoledronate (ZOL, purchased from Roche) inhibiting FPPS were mixed, and then incubated in the incubator in 5% $CO_2$ at 37° C. for 72 h to obtain positive control group cells (γδ-negative T cells). The ratio of the number of CFSE-labeled γδ-negative T cells to the number of K562 cells was 3:1, and the final concentration of Zoledronate in the culture system was 5 μM.

4. The experimental group cells, negative control group cells and positive control group cells were respectively detected for the fluorescence level of CFSE by flow cytometry. Specific steps are as follows. $2\times10^5$ experimental group cells, negative control group cells and positive control group cells were taken respectively, and 1 mL of Buffer (2% FBS in PBS) was added to these 3 groups of cells and then centrifuged, where the centrifugation parameters were set to at 2000 rpm, for 3 min and at room temperature. After centrifugation, the supernatant was discarded, the cells were resuspended in 200 μL of Buffer (2% FBS in PBS), and the fluorescence level of CFSE of the 3 groups of cells was detected on the machine.

Figure 4:
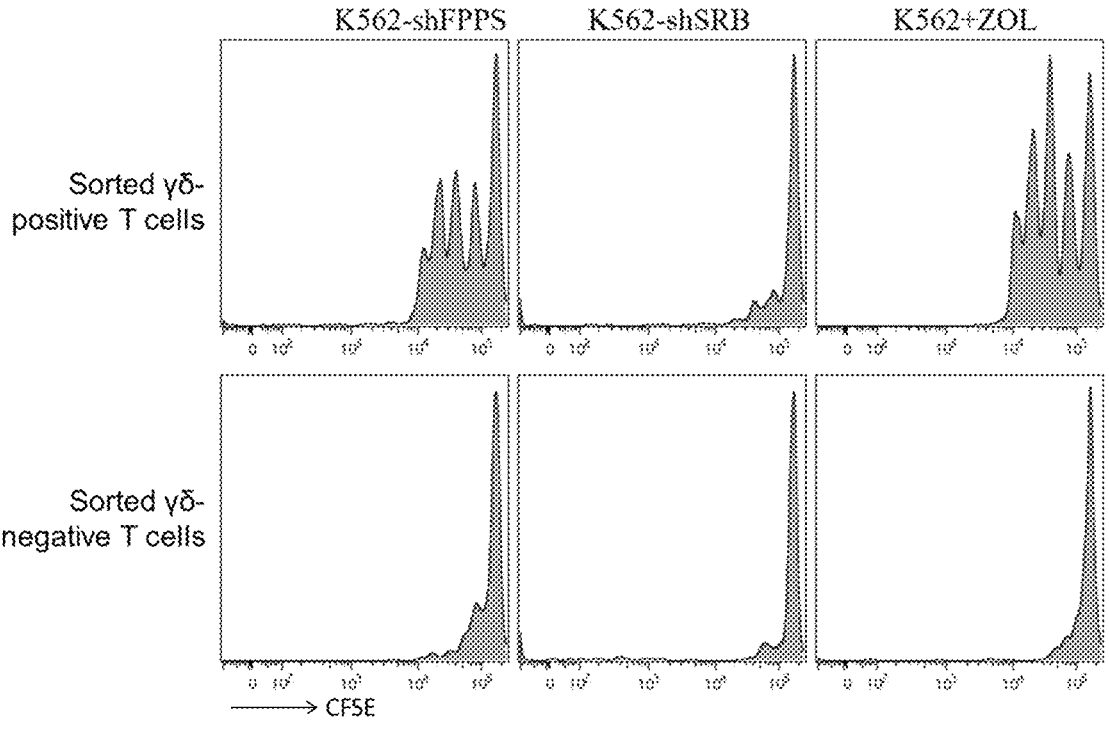
FIG. 4 shows the in vitro differentiation of γδ T cells stimulated by K562-shFPPS. CFSE labeled K562-shFPPS, K562-shSRB and K562 cells, respectively, and each kind of cells was mixed with the sorted γδ-positive T cells and γδ-negative T cells, where the number ratio of γδ T cells to K562 cells was 3:1, and 10 μM of Zoledronate was added to the K562 group as a positive control. After 72 h of culturing, the fluorescence intensity (abscissa) of the CFSE of different groups of cells was measured by flow cytometry.

The results are shown in FIG. 4. It can be seen from the figure that K562-shFPPS cells can effectively promote the differentiation of sorted γδ T cells.

5. Each group of cells continued to be cultured. When the cell concentration reached $(1.5-2)\times10^6$ cells/mL, amplification culturing was performed, and IL-2 was supplemented once to the culture system every 3 days to make the final concentration of IL-2 in the culture system 200 IU/mL.

6. When the cells were cultured to the 10th-14th day, 200 μL of cell suspension was taken for Trypan Blue counting, and cell identification, sorting and functional tests were performed subsequently.

The specific steps for Trypan Blue counting are as follows. 10 μL of fully dispersed cell suspension was taken, PBS was added to dilute the suspension to an appropriate multiple, 10 μL of Trypan Blue (purchased from Gibco, catalog No.: 15250-061) was added to the diluted cell suspension for staining, the suspension was pipetted evenly by a pipette, 10 μL of Trypan Blue stained cell suspension was pipetted into a hemocytometer covered with a glass slide, and the hemocytometer was observed under a 100× inverted microscope. Living cells were not stained, and dead cells were stained blue. The total number of cells in four squares was counted, then divided by 4, multiplied by the dilution multiple, multiplied by $10^4$, and finally multiplied by the total volume of the cell suspension to obtain the total number of cells.

The specific steps for identifying γδ T cells by flow cytometry are as follows. $(1-2)\times10^5$ experimental group cells, negative control group cells and positive control group cells were taken, respectively, 2 μL of biotin-labelled γδ T antibody (purchased from Biolegend, 331204) was added to each of the three groups of cell suspension and incubated at 4-8° C. for 10 min in the dark, 1 mL of Buffer (2% FBS in PBS) was added for resuspending and then centrifuged and washed, and then 2 μL of CD3-APC (purchased from BD, 555335), αβ-PE/CY7 (purchased from Biolegend, 306720), SA-PE (purchased from Biolegend, 405204) and 7AAD-PERCP (purchased from eBioscience, 00-6993-50) were added, incubated at 4-8° C. in the dark for 10 min, centrifuged and washed, and resuspended in 200 μL of Buffer. The γδ T ratio of the 3 groups of cells was detected by MACSQuant 10 flow cytometry (purchased from Miltenyi Biotechnology Co., Ltd., Germany), and analyzed by FlowJo.

Figure 5:
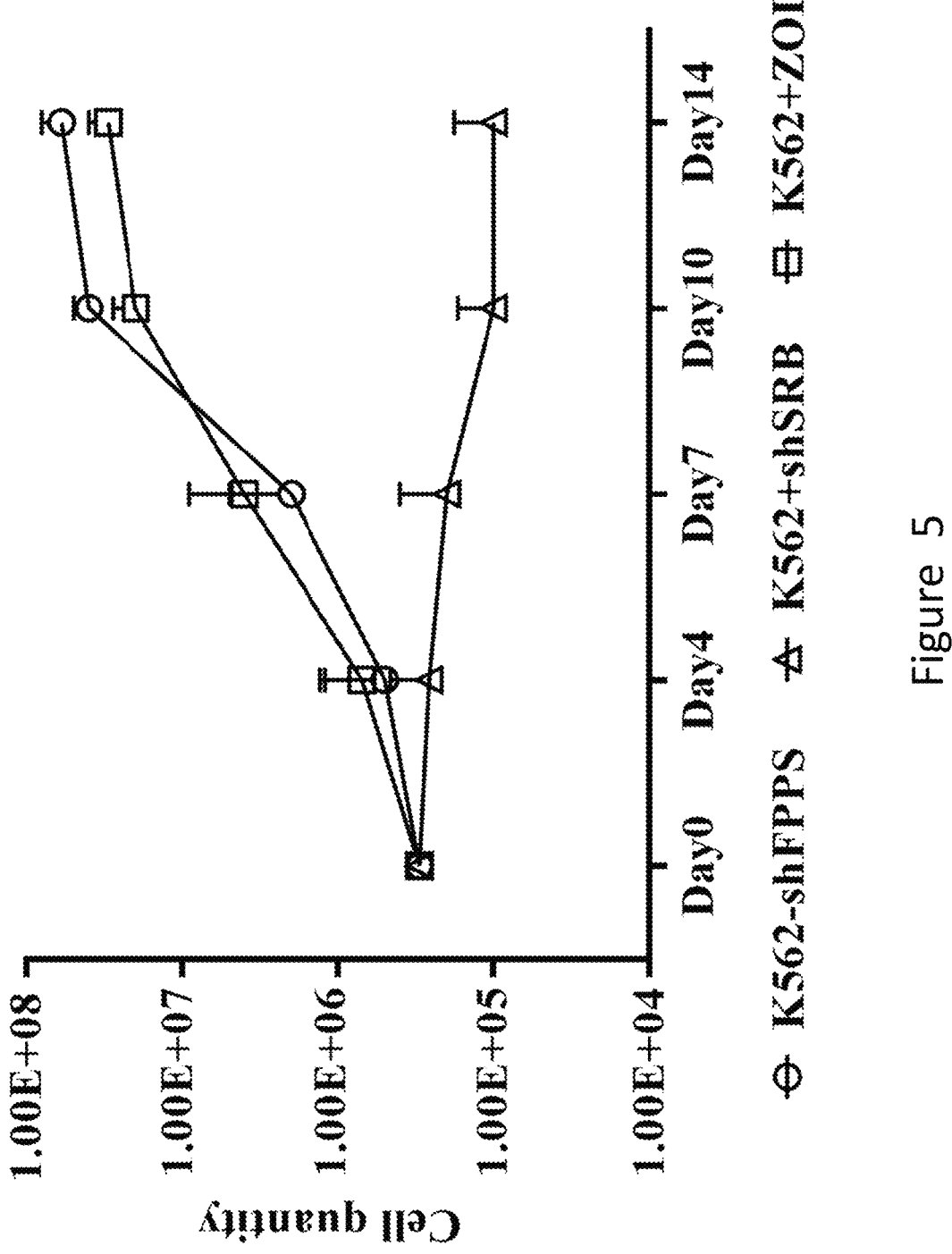
FIG. 5 shows that K562-shFPPS co-culturing enables a large-scale amplification of sorted γδ T cells. K562-shFPPS, K562-shSRB and K562 cells were mixed with the sorted γδ-positive T cells, and the number of cells at different times was counted. The ratio of the number of γδ-positive T cells to the number of K562-shFPPS or K562-shSRB or K562 cells was 5:1, and 10 μM of Zoledronate to the K562 group was added as a positive control.
Figure 6:
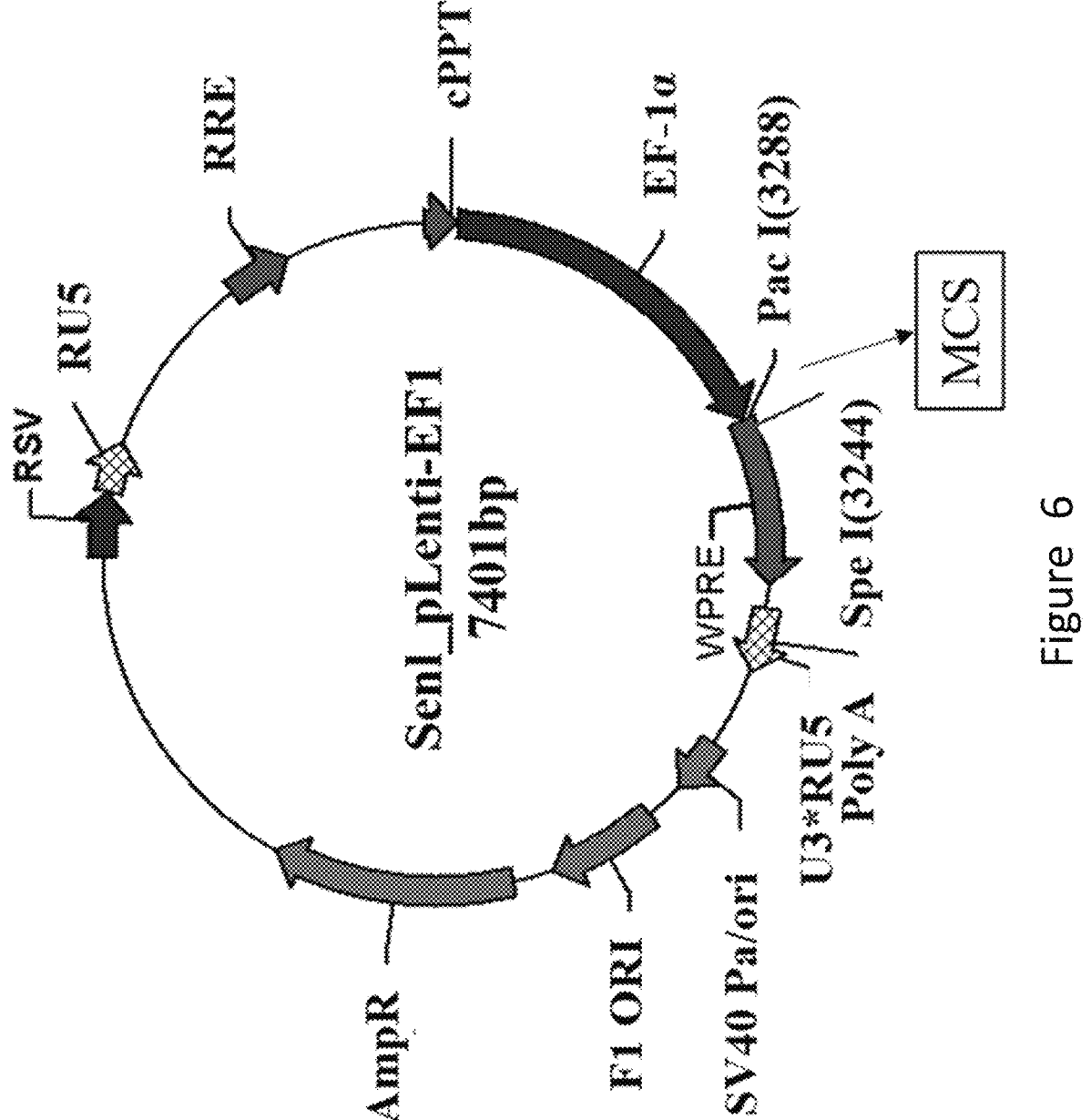
FIG. 6 shows the structure of the lentiviral plasmid carrying a CAR sequence.

The results are shown in FIG. 5. It can be seen from the figure that after 14 days of amplification culturing, the sorted γδ T cells can be amplified by more than 100 times under the stimulation of the K562-shFPPS cell line. It shows that tumor cell K562-shFPPS can promote the amplification of γδ T cells and increase the amplification efficiency of γδ T cells.

Example 2 Method for Producing CAR-γδ T Cells

I. Preparation of CAR22 Lentiviral Particles

In the present disclosure, a CAR structure is used to genetically modify γδ T cells. The CAR structure is, from the amino terminus to the carboxyl terminus, as follows: ScFv(CD22)-Hinge(CD8)-TM(CD8)-CD137-CD3ζ, that is, from the amino terminus to the carboxyl terminus are sequentially: a single-chain variable region derived from the CD22 monoclonal antibody (clone ID: M971), a CD8a hinge region and a transmembrane region, a CD137 signal domain and a CD3ζ chain intracellular region. Its amino acid sequence is shown in SEQ ID No. 3 in the sequence list, and its nucleotide sequence is shown in SEQ ID No. 4 in the sequence list. The DNA molecule as shown in SEQ ID No. 4 was inserted between restriction enzyme sites PacI and SpeI of the Senl_pLenti-EF1 vector (the Senl_pLenti-EF1 vector is a vector obtained by adding restriction enzyme sites PacI and SpeI on both sides of the original plasmid cloning site, and the original plasmid is named LV-pRRLEF1.WPRE and is provided by Cyagen Biosciences Inc., with the contract No.: S1002079) to obtain the CAR22 lentiviral vector.

The CAR22 lentiviral vector was packaged according to the method in step 2 of Step I in Example 1 to obtain CAR22 lentiviral particles.

II. Preparation of CAR-γδ T Cells

1. Isolating and Sorting of γδ T Cells (Day 0)

50-100 mL of venous blood was aseptically collected from a healthy adult, and peripheral blood mononuclear cells (PBMCs) were obtained by density gradient centrifugation. γδ T cells were sorted from PBMCs by using the γδ T cell sorting kit (purchased from Miltenyi Biotechnology Co., Ltd., Germany, catalog No.: 130-092-892) to obtain the γδ T cells.

2. Culturing of γδ T Cells

The γδ T cells sorted in step 1 were resuspended in TexMACS™ medium containing 200 U/ml recombinant human IL-2 to obtain a γδ T cell culture system, which was divided into the following groups according to the composition of the culture system for culturing:

K562-shFPPS group: K562-shFPPS cells were added to the γδ T cell culture system, and the ratio of the number of γδ T cells to the number of K562-shFPPS cells was 3:1;

K562+ZOL group: K562 cells and ZOL were added to the γδ T cell culture system, the ratio of the number of γδ

T cells to the number of K562 cells was 3:1, and the final concentration of ZOL in the culture system was 200 IU/mL; and PBMC+ZOL group: ZOL was added to PBMC cells, and the final concentration of ZOL in the culture system was 10 μM.

The cells were plated into a 24-well plate at $5 \times 10^5$ γδ T cells/500 μL medium/well, placed in the cell incubator and cultured in 5% $CO_2$ at 37° C. for 2 days.

3. Transfection of Lentivirus to Cells (Day 2)

After 2 days of culturing, CAR22 lentiviral particles were transfected to each group of cells. The specific steps of transfection are as follows. The 24-well plate was taken out of the cell incubator in advance, and 10‰ Protamine sulfate (purchased from Sigma Co., product catalog No.: P3369-10G) and 5 μL of CAR22 lentiviral particle solution were added to each well, mixed by drawing the "8" on the operating table and then pipetted by a pipette. The above solution was centrifuged at 35° C., at 2000 rpm and for 2 h. After centrifugation, the 24-well plate was taken out of the centrifuge and placed into the cell incubator in 5% $CO_2$ at 37° C. for continuous culturing.

4. Amplification Culturing (Day 3-14)

After 3 days of culturing, half of the medium was refreshed, that is, the 24-well plate was taken out of the incubator, half of the supernatant was aspirated from each well, and the DMEM complete medium was added to replace the aspirated supernatant, and then the culturing continued. When the cell concentration reached $(1.5-2) \times 10^6$/ml, the cells were transferred to a flask or bag, and 200 IU/ml IL-2 was supplemented once every 2 days. When the cells were cultured to the 10th-14th day, 200 μL of cell suspension was taken for Trypan Blue counting, and cell identification, sorting and functional tests were performed subsequently.

III. Detection of CAR-γδ T Cells by Flow Cytometry

1. Preparation of Biotin-Labeled CD22-Fc

100 μg of purified CD22-Fc protein powder (purchased from Sino Biological Inc., catalog No.: 11958-H02H) was taken and resuspended in PBS at pH 7.2 to make the final concentration of CD22-Fc protein powder (0.5-1) μg/μL. Dimethyl sulfoxide (DMSO) with a purity >99.9% was used to dissolve an appropriate amount of biotin (purchased from US Everbright Inc. catalog No.: B5026-1) to prepare a 2 mM biotin suspension. The above two were mixed at a molar ratio of CD22-Fc protein:biotin=1:10, then left stand at room temperature for 1 h, and mixed once again every 15 min. Desalination was performed by using a desalting column (operation steps were referred to the instructions of the desalting column) to obtain the biotin-labeled CD22-Fc, where according to different volumes, the desalting column PD-10 (purchased from General Electric Company, US, catalog No.: 17-0851-01) or the desalting column G-25 (purchased from General Electric Company, US, catalog No.: 28-9180-04) could be chosen.

2. Detection of the Cell Surface Expression Level of CAR (CD22) by Flow Cytometry After 48-72 h of lentiviral transfection, each group of cells was taken to detect the transfection efficiency (transfection efficiency was calculated as the percentage of γδ T cells that were positive for CD22-Fc labeling in all γδ T cells). Specific step are as follows. Each tube of $(1-2) \times 10^5$ cells was added with 1 μL of biotin-labeled CD22-Fc and incubated at 4-8° C. for 10 min in the dark, and 1 mL of (PBS+2% FBS) was added for resuspending and then centrifuged and washed. SA-PE, CD3-APC, CD4-PE-Cy7, CD8-VioBlue and 7AAD (purchased from Miltenyi Biotechnology Co., Ltd., Germany) were added to each, incubated at 4-8° C. in the dark for 10 min, centrifuged and washed, and resuspended in 200 μL of Buffer, and the CAR (CD22) expression level was detected by MACSQuant 10 flow cytometry and analyzed by FlowJos.

Figure 7:
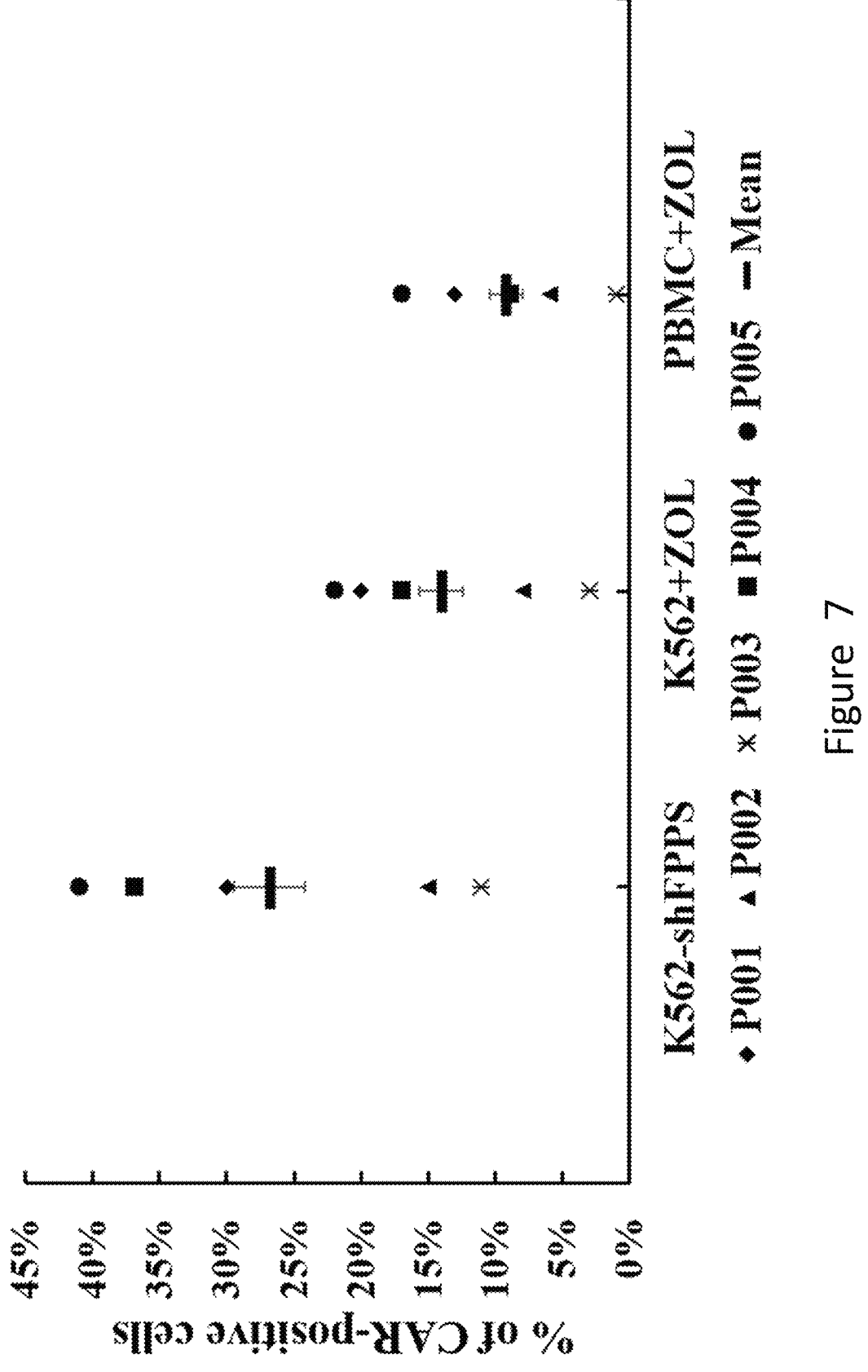
FIG. 7 shows that the co-culturing of K562-shFPPS and sorted γδ T cells can significantly improve the transfection efficiency of the CAR.

The detection results are shown in FIG. 7. It can be seen from the figure that the transfection efficiency of the K562-shFPPS group was significantly higher than that of the K562+ZOL group and the PBMC+ZOL group. It shows that the tumor cell K562-shFPPS can improve the transfection efficiency of lentivirus to γδ T cells.

IV. Sorting and Purification of CAR-γδ-Positive T Cells

The CAR22-modified γδ T cells cultured to the 7th-10th day according to the above method were sorted and purified to obtain purified CAR-γδ-positive T cells. Specific steps are as follows. CAR-γδ T cells cultured to the 7th-10th day were collected and then centrifuged, and the supernatant was discarded. At the ratio that every $1\times10^7$ CAR-γδ T cells was added with 80 μL of buffer (PBS+2% FBS) and 5 μL of biotin-labeled CD22-Fc, the buffer and biotin-labeled CD22-Fc were added, and then incubated at 4-8° C. for 15 min in the dark. After the incubation, at a ratio that every $1\times10^7$ CAR-γδ T cells was added with 1-2 mL of buffer solution, the buffer solution was added, and then centrifuged and washed. After washing, at a ratio that every $1\times10^7$ CAR-γδ T cells was added with 80 μL of buffer solution (PBS+2% FBS) and 10 μL of SA magnetic beads, the buffer and SA magnetic beads were added, mixed well, and incubated at 4-8° C. for 30 min in the dark. After the incubation, the buffer solution was added at a ratio that every $1\times10^7$ CAR-γδ T cells was added with 1-2 mL of buffer solution, and then centrifuged and washed. The cell precipitate layer was pipetted and mixed with 500 μL of buffer solution per $1\times10^8$ cells, and CAR-γδ-positive T cells were sorted by using a magnetic sorting column, that is, the dropped cell suspension was the sorted CAR-γδ-negative T cells, which were denoted as CAR-γδ T cells, and the cells left in the magnetic column were CAR-γδ-positive T cells, which were denoted as CAR+γδ T cells. The sorted positive cells were collected and counted, and the purity of CAR-positive T cells was detected by flow cytometry. The remaining cells continued to be cultured or directly used for subsequent functional tests.

V. In Vitro Functional Test of CAR-γδ T Cells

1. Construction of Target Cell Strains (1) K562-CD22 Cells

In order to construct a tumor cell strain expressing the specific antigen CD22, a CD22 full-length cDNA sequence (Genebank, No.: NM_001771.3) was cloned from the PBMC of healthy persons, and the CD22 full-length cDNA sequence was inserted into a U6-based shRNA Knockdown lentiviral plasmid which carries the Puromycine resistance gene (purchased from Cyagen Biosciences Inc.) to obtain the lentiviral plasmid. The lentiviral plasmid was packaged and transfected into K562 cells according to the methods in Step 2 and 3 of Step I of Example 1, and K562-CD22 cells with higher purity were obtained after screening.

(2) K562-CD19 Cells

In order to construct a tumor cell strain expressing the specific antigen CD19, a CD19 full-length cDNA sequence (Genebank, No.: NM_001770.5) was cloned from the PBMC of healthy persons, and the CD19 full-length cDNA sequence was inserted into a U6-based shRNA Knockdown lentiviral plasmid which carries the Puromycine resistance gene (purchased from Cyagen Biosciences Inc.) to obtain the lentiviral plasmid. The lentiviral plasmid was packaged and transfected into K562 cells according to the methods in Step 2 and 3 of Step I of Example 1, and K562-CD19 cells with higher purity were obtained after screening and used as negative control.

(3) LCL Cells

LCL cells are immortal cell lines obtained by infecting peripheral B cells of healthy adults with EB virus, and express the CD22 antigen on the cell surface. The specific preparation method is as follows. B95.8 cells (purchased from the Cell Bank of the Chinese Academy of Sciences) were inoculated into a T75 cm$^2$ cell culture flask at a concentration of $3\times10^5$ cells/mL, and the medium was RPMI1640 (purchased from gibco, product catalog No.: 22400-088)+10% FBS (purchased from gibco, catalog No.: 10099141). After 48 h of culturing in the incubator in 5% $CO_2$ at 37° C., the cells were re-inoculated at a concentration of $1\times10^6$ cells/mL, and TPA with a final concentration of 20 ng/mL (purchased from cayman, catalog No.: 16561-29-8) was added to process cells. 1 h later, the cells were washed with an RPMI1640 complete medium three times to remove the TPA. The obtained cells were re-inoculated at a concentration of $1\times10^6$ cells/mL and cultured in the incubator in 5% $CO_2$ at 37° C. for 96 h, the culture solution was collected into a 50 mL centrifuge tube and centrifuged at 4° C., 600 g for 10 min, and the supernatant was filtered through a 0.45 μm filter. The filtrate was the EBV virus suspension. Peripheral blood mononuclear cells (PBMCs) obtained by density gradient centrifugation were sorted by using CD3 (purchased from Miltenyi Biotechnology Co., Ltd., Germany, catalog No.: 130-050-101). The obtained CD3-cells, namely B cells, were inoculated into a culture flask at a concentration of $3\times10^5$ cells/mL, and 1/10 volume of EBV virus suspension was added. One week after EBV virus infection, cell clusters could be seen under an inverted microscope, that is, successfully transformed LCL cells. As time goes by, cell clusters became larger and larger, and could be amplified and frozen according to the number of cells and the color of the medium.

2. Detection of Expression Level of Cytokine IFN-γ and Surface CD137 by Flow Cytometry The target cell strain obtained in step 1 was added to a 96-well U-bottom cell culture plate at a quantity of $1\times10^4$ per well; the corresponding quantities of sorted and purified CAR-γδ-positive T cells were added to the corresponding wells at a ratio of effector cells (CAR-γδ-positive T cells): target cells of 10:1, 3:1 and 1:1 respectively. Effector cell and target cell blank control wells were set respectively, CAR-γδ-negative T cells were used as control effector cells, and the same detection was set up. The cell culture plate was placed in the incubator and co-cultured in 5% $CO_2$ at 37° C. for 4 h, the cell suspension was aspirated and washed twice with PBS, the cells were resuspended in 100 μL of buffer, and 2 μL of CD3-APC-Cy7 and CD4-PE.Cy7, CD8-VioBlue and CD137-PE (BD company, clone ID: 4B4-1) were added respectively, incubated at 4-8° C. in the dark for 10 min, washed, and then stained by using an intracellular staining kit (catalog No.: 554714) available from BD Co., where staining method was referred to the instruction. After the corresponding reagent penetrated the cell membrane, 5 μL of mouse anti-human IFN-γ-FITC monoclonal antibody (BD Co., clone ID: B27) was added, incubated at 4-8° C. in the dark for 10 min and then washed. After washing, the expression levels of IFN-γ and CD137 were detected by flow cytometry.

Figure 8:
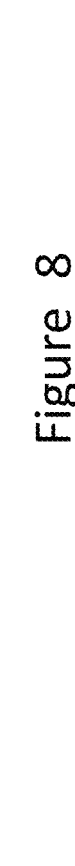
FIG. 8 shows that CAR+γδ T cells produced by co-culturing K562-shFPPS specifically respond to CD22-expressing cells, secrete more IFN-γ and express more CD137 on the cell surface.

The detection results are shown in FIG. 8. It can be seen from the figure that CAR+γδ T cells produced by co-culturing of K562-shFPPS cells and γδ T cells responded specifically to the CD22-expressing tumor cells, secreted more IFN-γ, and expressed more CD137 on the cell surface.

3. Detection of Specific Killing Activity of CAR-γδ T Cells by Flow Cytometry

Each target cell strain in step 1 was labeled by CFSE according to the method in step 2 of step II of Example 1 and incubated at room temperature or 37° C. for 20 min in the dark, and 5 volumes of medium containing 10% (volume fraction) FBS was added to terminate staining. The above was centrifuged at 2000 rpm for 5 min, the cells were resuspend after centrifugation and incubated at room temperature or 37° C. for 10 min in the dark. After the incubation, the cells were washed twice and resuspended for later use. The CFSE-labeled target cells were added to a 96-well cell culture plate at a density of $1 \times 10^4$ cells/well; the corresponding quantities of sorted and purified CAR-γδ T positive cells were added to the corresponding wells at a ratio of effector cells (CAR-γδ-positive T cells):target cells of 10:1, 3:1 and 1:1 respectively. Blank control wells of effector cells and target cells were set respectively, CAR-γδ-negative T cells were used as control effector cells, and the same detection was set up. The cell culture plate was placed in the incubator and co-cultured in 5% $CO_2$ at 37° C. for 4 h, the cell suspension was aspirated and washed twice with PBS, the cells were resuspended in 100 μL of buffer, added with 5 μL of 7-AAD, incubated in the dark for 10 min and then washed. After washing, the killing rate was detected by flow cytometry, where the killing rate was the percentage of killed target cells (CFSE+7AAD+) to all target cells (CSFE+).

Figure 9:
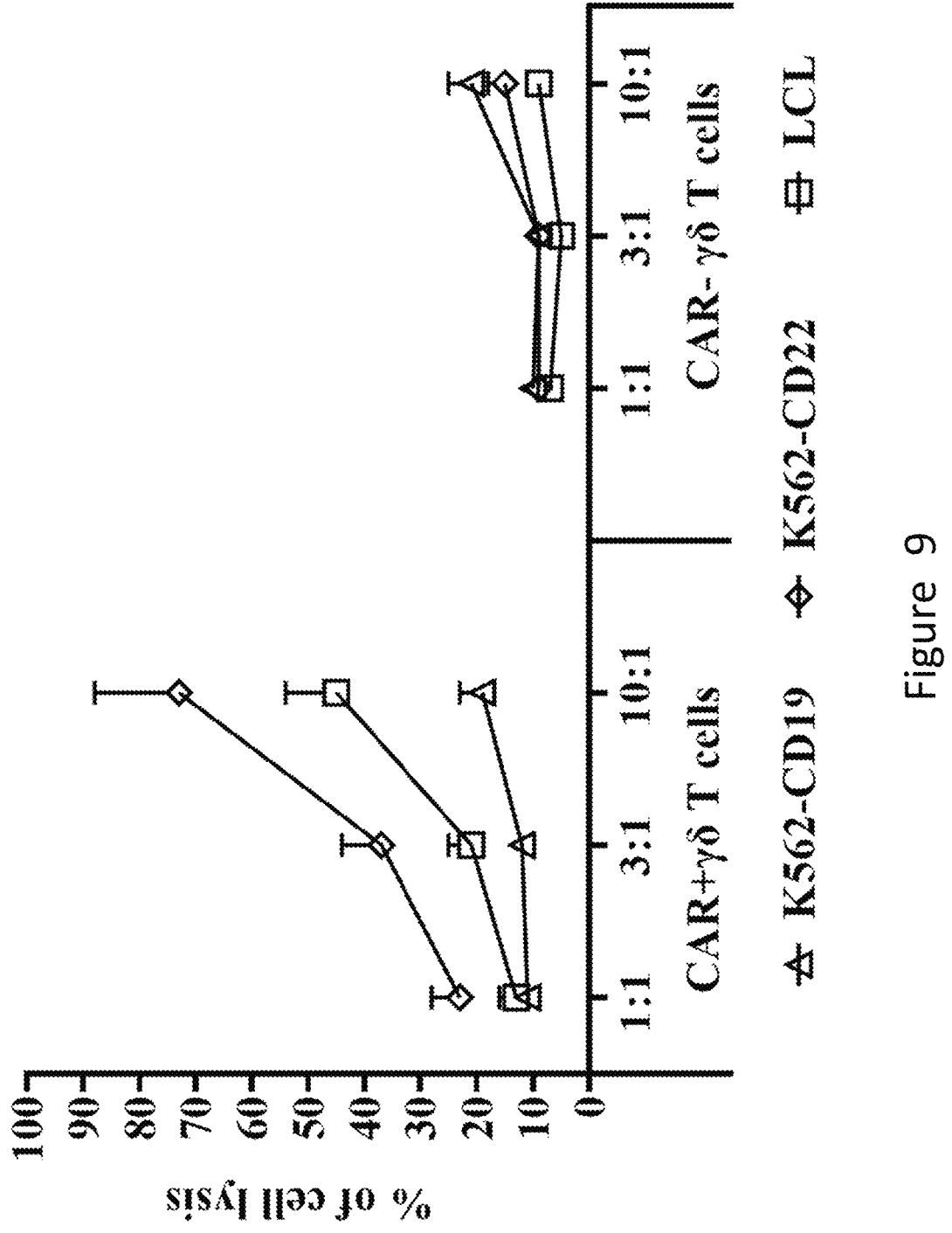
FIG. 9 shows that CAR+γδ T cells produced by co-culturing K562-shFPPS can specifically lyse CD22-expressing tumor cells.

The results are shown in FIG. 9. It can be seen from figure that CAR+γδ T cells produced by co-culturing of K562-shFPPS cells and γδ T cells can specifically lyse the CD22-expressing tumor cells.

INDUSTRIAL APPLICATION

In order to overcome the shortcomings of the existing art, the present disclosure provides a brand new γδ T cell amplification solution, and the solution is specifically as follows: transfecting K562 cells with shFPPS targeted to FPP synthase (FPPS) by means of a lentiviral vector, such that the expression of FPPS in the K562 cells is lowered and a K562-shFPPS cell line with reduced FPPS expression is constructed; adding the K562-shFPPS cell line into a γδ T cell culture system for co-culturing with the γδ T cells, where it is found that the K562-shFPPS cell line can directly stimulate in vitro differentiation and amplification of purified Vγ9δ2 T cells; and adding a CAR-expressing lentiviral vector to the γδ T cell culture system containing the K562-shFPPS cell line for co-culturing, where it is found that the K562-shFPPS cell line can further effectively improve the transfection rate of CAR genes, thereby improving the preparation efficiency of CAR-γδ T cells. The above experimental results show that the K562-shFPPS cell line can effectively improve the in vitro amplification capability of γδ T cells and the transfection rate of CAR genes, and the solution provided in the present disclosure effectively overcomes the technical challenge of the large-scale production of CAR-γδ T cells, and has a good application prospect.

---

What is claimed is:

1. A method for expanding γδ T cells, comprising:

introducing shRNA that inhibits the expression of FPPS (Farnesyl pyrophosphate Synthase)-encoding gene into tumor cells to obtain tumor cells with reduced FPPS expression and activity;

adding the tumor cells with reduced FPPS expression and activity to a γδ T cell culture system, wherein the shRNA that inhibits the expression of FPPS-encoding gene is single-stranded RNA comprising in 5' to 3' order: a stem I, a loop and a stem II;

wherein the stem I consists of the sequence of positions 1-21 of SEQ ID NO: 2; the loop consists of the sequence of positions 22-27 of SEQ ID NO: 2; and the stem II consists of the sequence of positions 28-48 of SEQ ID NO: 2.

2. The method according to claim 1, wherein a ratio of the number of the γδ T cells to the number of the tumor cells with reduced FPPS expression and activity is (1-10):1.

3. A method for producing CAR-γδ T cells, comprising:

a) introducing shRNA that inhibits the expression of FPPS (Farnesyl pyrophosphate Synthase)-encoding gene into tumor cells to obtain tumor cells with reduced FPPS expression and activity; adding the tumor cells with reduced FPPS expression and activity to a γδ T cell culture system and culturing to obtain a mixed culture system; and b) adding a vector encoding a chimeric antigen receptor (CAR) to the mixed culture system and culturing to obtain CAR-γδ T cells, wherein the shRNA that inhibits the expression of FPPS-encoding gene is single-stranded RNA comprising in 5' to 3' order a stem I, a loop and a stem II;

wherein the stem I consists of the sequence of positions 1-21 of SEQ ID NO: 2; the loop consists of the sequence of positions 22-27 of SEQ ID NO: 2; and the stem II consists of the sequence of positions 28-48 of SEQ ID NO: 2.

4. The method according to claim 3, wherein in step a), a ratio of the number of the γδ T cells to the number of the tumor cells with reduced FPPS expression and activity is (1-10):1.

5. The method according to claim 3, wherein in step b), the vector encoding the chimeric antigen receptor is a lentiviral vector.

6. A method for tumor immunotherapy, comprising:

a) producing CAR-γδ T cells according to the method of claim 3; and b) transfusing the CAR-γδ T cells into a tumor patient, wherein said CAR-γδ T cells recognize and kill tumor cells in said patient, thereby treating said patient.

7. The method according to claim 1, wherein the tumor cells are a chronic myelogenous leukemia cell line.

8. The method according to claim 7, wherein the chronic myelogenous leukemia cell line is K562 cells.

9. The method according to claim 3, wherein the tumor cells are a chronic myelogenous leukemia cell line.

\* \* \* \* \*